United States Patent
Bischoff et al.

(10) Patent No.: US 6,656,734 B1
(45) Date of Patent: Dec. 2, 2003

(54) COMPOSITIONS FOR THE DELIVERY OF POLYNUCLEOTIDES TO CELLS

(75) Inventors: Rainer Bischoff, Barsebacksby (SE); Hanno Kolbe, Achenheim (FR); Klaus Schughart, Kenzingen (DE)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/107,271

(22) Filed: Jun. 30, 1998

(30) Foreign Application Priority Data

Jul. 1, 1997 (FR) ............................. 97 08267
Oct. 16, 1997 (FR) ............................. 97 12950

(51) Int. Cl.$^7$ .............................................. C12N 15/87
(52) U.S. Cl. ....................... 435/455; 435/458; 435/461; 536/23.1; 536/23.2; 536/23.5; 536/24.1
(58) Field of Search ........................ 424/486; 556/137; 514/44; 435/455, 458, 461; 536/23.1, 23.2, 23.5, 24.1

(56) References Cited

U.S. PATENT DOCUMENTS

| | | | |
|---|---|---|---|
| 4,711,955 A | | 12/1987 | Ward et al. ............... 536/25.32 |
| 5,028,726 A | * | 7/1991 | Farrell ........................ 556/137 |
| 5,525,711 A | | 6/1996 | Hawkins et al. ............ 536/23.1 |
| 5,714,166 A | * | 2/1998 | Tomalia ...................... 424/486 |
| 5,854,224 A | * | 12/1998 | Lockett ........................ 514/44 |
| 6,303,379 B1 | * | 10/2001 | Selden et al. ............... 435/455 |

FOREIGN PATENT DOCUMENTS

| | | | | |
|---|---|---|---|---|
| EP | 0 392 175 | | 10/1990 | |
| WO | WO95/26718 | | 10/1985 | |
| WO | WO94/19469 | | 9/1994 | |
| WO | WO 95/26718 | * | 10/1995 | .................. 514/44 |
| WO | WO97/00957 | | 1/1997 | |
| WO | WO97/18841 | | 5/1997 | |

OTHER PUBLICATIONS

Lewis L. Coriell, Methods in Enzymology, vol. LVIII, pp. 29–36, 1979.*
Melkonyan et.al.; Electroporation efficiency in mammalian cells is increased by dimethyl sulfoxide (DMSO), 1996, Nucleic Acids Research vol. 24: 4356–4357.*
Saxe III et.al.; The cAMP Receptor Subtype cAR2 Is Restricted to a Subset of Prestalk Cells during Dictyostelium . . . Unexpected DIF–1 Responsiveness; 1996, Developmental Biology 174: 202–213.*
Medline, Accession No. 89075362, 1988.*
Hart et. al.; Hum. Mol. Gen. 4(9): 1597–1602, 1995.*
Sugimoto et. al.; Bio/Technology 12(7): 694–698. 1994.*
Sawai et. al. Am. J. Repr. Immunol. 34(1): 26–34, 1995.*
Mittal et al (Virus Research 28(1): 67–90, abstract only, Apr. 1993.*
Burns et al (Anal. Biochem. 162(2): 399–404, abstract only, May 1987.*

Ambinder, Richard F. et al., "Functional Domains of Epstein–Barr Virus Nuclear Antigen EBNA–1." Journal of Virology (Mar. 1991), pp. 1466–1478.
Anderson, W. French, "Human Gene Therapy." Science, vol. 256 (May 8, 1992), pp. 808–813.
Aubin, Rémy J. et al., "Factors Influencing Efficiency and Reproducibility of Polybrene–Assisted Gene Transfer." Somatic Cell and Molecular Genetics, vol. 14, No. 2 (1988), pp. 155–167.
Behr, Jean Paul et al., "Efficient gene transfer into mammalian primary endocrine cells with lipopolyamine–coated DNA." Proc. Natl. Acad. Sci. USA, vol. 86 (Sep. 1989), pp. 6982–6986.
Colbère–Garapin, Florence et al., "A New Dominant Hybrid Selective Marker for Higher Eukaryotic Cells." J. Mol. Biol. (1981) 150, pp. 1–14.
Cotten, Matt et al., "Non–viral approaches to gene therapy." Current Opinion in Biotechnology, 4 (1993), pp. 705–710.
Felgner, Jiin et al., "Cationic Lipid–Mediated Delivery of Polynucleotides." Methods: A Companion to Methods in Enzymology, 5 (1993), pp. 67–75.
Felgner, Philip L. et al., "Lipofection: A highly efficient, lipid–mediated DNA–transfection procedure." Proc. Natl. Acad. Sci. USA, vol. 84 (Nov. 1987), pp. 7413–7417.
Gao, Xiang et al., "A Novel Cationic Liposome Reagent for Efficient Transfection of Mammalian Cells." Biochemical and Biophysical Research Communications, vol. 179, No. 1 (1991), pp. 280–285.
Giordano, Frank J., "Intracoronary gene transfer of fibroblast growth factor–5 increases blood flow and contractile function in an ischemic region of the heart." Nature Medicine, vol. 2, No. 5 (May 1996), pp. 534–539.
Johnson, Carl R. et al., "Methyl Phenyl Sulfoxide." Organic Synthesis, Collective vol. 5 (1973), pp. 791–793.
Haensler, Jean et al., "Polyamidoamine Cascade Polymers Mediate Efficient Transfection of Cells in Culture." Bioconjugate Chem, vol. 4, No. 5 (1993), pp. 372–379.

(List continued on next page.)

Primary Examiner—Dave T. Nguyen
Assistant Examiner—Richard Schnizer
(74) Attorney, Agent, or Firm—Burns, Doane, Swecker & Mathis, L.L.P.

(57) ABSTRACT

The present invention relates to a composition which is intended for transferring at least one therapeutically active substance into the interior of a target cell, characterized in that it comprises a mixture of at least one therapeutically active substance and at least one polar compound which is selected from a specific group of aprotic polar compounds. The therapeutically active substance is preferably a polynucleotide, and the polar compound is DPSO, which improves the ability of the polynucleotide to be transfected into the interior of the cells. The compositions according to the invention can be used as a diagnostic therapeutic, prophylactic or vaccinal medicament for treating the human or animal body by means of gene therapy.

18 Claims, 5 Drawing Sheets

OTHER PUBLICATIONS

Hartman, Standish C. et al., "Two dominant-acting selectable markers for gene transfer studies in mammalian cells." Proc. Natl. Acad. Sci. USA, vol. 85 (Nov. 1988), pp. 8047–8051.

Isner, Jeffrey M. et al., "Clinical evidence of angiogenesis after arterial gene transfer of phVEGF$_{165}$ in patient with ischaemic limb." The Lancet, vol. 348 (Aug. 10, 1996), pp. 370–374.

Lanford, Robert E. et al., "Construction and Characterization of an SV40 Mutant Defective in Nuclear Transport of T Antigen." Cell, vol. 37 (Jul. 1984), pp. 801–813.

Lowry, Israel et al., "Isolation of Transforming DNA: Cloning the Hamster aprt Gene." Cell, vol. 22 (Dec. 1980), pp. 817–823.

McCoy, Ronald D. et al., "Pulmonary Inflammation Induced by Incomplete or Inactivated Adenoviral Particles." Human Gene Therapy, 6 (Dec. 1995), pp. 1553–1560.

McLachlan, G. et al., "Evaluation in vitro and in vivo of cationic liposome–expression construct complexes for cystic fibrosis gene therapy." Gene Therapy, 2 (1995), pp. 614–622.

Meyer, K.B. et al., "Intratracheal gene delivery to the mouse airway: characterization of plasmid DNA expression and pharmacokinetics." Gene Therapy, 2 (1995), pp. 450–460.

Mühlhauser, Judith et al., "VEGF$_{165}$ Expressed by a Replication–Deficient Recombinant Adenovirus Vector Induces Angiogenesis In Vivo." Circulation Research, vol. 77, No. 5 (Nov. 1995), pp. 1077–1086.

Mulligan, R.C. et al., "Selection for animal cells that express the *Escherichia coli* gene coding for xanthine–guanine phosphoribosyltransferase." Proc. Natl. Acad. Sci. USA, vol. 78, No. 4 (Apr. 1981), pp. 2072–2076.

O'Hare, K. et al., "Transformation of mouse fibroblasts to methotrexate resistance by a recombinant plasmid expressing a prokaryotic dihydrofolate reductase." Proc. Natl. Acad. Sci. USA, vol. 78, No. 3 (Mar. 1981), pp. 1527–1531.

Oudrhiri, Noufissa et al., "Gene transfer by guanidinium-cholesterol cationic lipids into airway epithelial cells in vitro and in vivo." Proc. Natl. Acad. Sci. USA, vol. 94 (Mar. 1997), pp. 1651–1656.

Plank, Christian et al., "The Influence of Endosome–disruptive Peptides on Gene Transfer Using Synthetic Virus–like Gene Transfer Systems." The Journal of Biological Chemistry, vol. 269, No. 17 (Apr. 29, 1994), pp. 12918–12924.

Rhim, Johng S. et al., "Neoplastic transformation of human keratinocytes by Polybrene–induced DNA–mediated transfer of an activated oncogene." Oncogene, 4 (1989), pp. 1403–1409.

Riessen, Reimer et al., "Arterial Gene Transfer Using Pure DNA Applied Directly to a Hydrogel–Coated Angioplasty Balloon." Human Gene Therapy, 4 (1993), pp. 749–758.

Rommens, Johanna et al., "Identification of the Cystic Fibrosis Gene: Chromosome Walking and Jumping." Science, vol. 245 (Sep. 8, 1989), pp. 1059–1065.

Rose, Robert B. et al., "Three–Dimensional Structures of HIV–1 and SIV Protease Product Complexes." Biochemistry, 35 (1996, pp. 12933–12944.

Rosenfeld, Melissa A. et al., "Impact of basic research on tomorrow's medicine." Chest, 109 (1996), pp. 241–252.

Rutenber, Earl E. et al., "A New Class of HIV–1 Protease Inhibitor: The Crystallographic Structure, Inhibition and Chemical Synthesis of an Aminimide Peptide Isostere." Bioorganic & Medicinal Chemistry, vol. 4, No. 9 (1996), pp. 1545–1558.

Santerre, Robert F. et al., "Expression of prokaryotic genes for hygromycin B and G418 resistance as dominant–selection markers in mouse L cells." Gene, 30 (1984), pp. 147–156.

Schaper, Wolfgang et al., "Molecular Mechanisms of Coronary Collateral Vessel Growth." Circulation Research, 79 (1996), pp. 911–919.

Schaper, Wolfgang et al., "Therapeutic targets in cardiovascular disorders." Current Opinion in Biotechnology, 7 (1996), pp. 635–640.

Scheule, Ronald K. et al., "Basis of Pulmonary Toxicity Associated with Cationic Lipid–Mediated Gene Transfer to the Mammalian Lung." Human Gene Therapy, 8 (Apr. 10, 1997), pp. 689–707.

Smith, P.K. et al., "Measurement of Protein Using Bicinchoninic Acid." Analytical Biochemistry, 150 (1985), pp. 76–85.

Szybalska, Elizabeth Hunter et al., "Genetics of Human Cell Lines, IV. DNA–Mediated Heritable Transformation of a Biochemical Trait." Proc. Natl. Acad. Sci. USA, vol. 48, No. 12 (Dec. 1962), pp. 2026–2034.

Wang, Qing et al., "Second–generation adenovirus vectors." Nature Medicine, vol. 2, No. 6 (Jun. 1996), pp. 714–716.

Wigler, Michael et al., "Transfer of Purified Herpes Virus Thymidine Kinase Gene to Cultured Mouse Cells." Cell, vol. 11 (May 1977), pp. 223–232.

Wigler, M. et al., "Transformation of mammalian cells with an amplifiable dominant–acting gene." Proc. Natl. Acad. Sci. USA, vol. 77, No. 6 (Jun. 1980), pp. 3567–3570.

Wolff, Jon A. et al., "Direct Gene Transfer into Mouse Muscle in Vivo." Science, vol. 247 (Mar. 23, 1990), pp. 1465–1468.

Yang, Yiping et al., "MHC Class I–Restricted Cytotoxic T Lymphocytes to Viral Antigens Destroy Hepatocytes in Mice Infected with E1–Deleted Recombinant Adenoviruses." Immunity, vol. 1 (Aug. 1994), pp. 433–442.

Aubin et al, "Polybrene/DMSO–Assisted Gene Transfer", *Molecular Biotechnology* vol. 1, pp. 29–47 (1994).

Rhim et al., "Neoplastic Transformation of Human Keratinocytes by Polybrene–Induced DNA–Mediated Transfer of an Activated Oncogene", *Oncogene* vol. 4, pp. 1403–1409 (1989).

K. Schughart et al, *Human Gene Therapy*, "Solvoplex: A New Type of Synthetic Vector for Intrapulmonary Gene Delivery", vol. 10, p. 2891–2905 (Dec. 10, 1999).

\* cited by examiner

COMPOSITIONS FOR THE DELIVERY OF POLYNUCLEOTIDES TO CELLS

FIELD OF THE INVENTION

The present invention relates to a composition which can be used for introducing a therapeutically active substance into a target cell, in particular a vertebrate cell, more specifically a mammalian cell. More specifically, the present invention relates to the use of this composition for preparing a vector for transferring a therapeutically active substance, in particular a polynucleotide, into a target cell.

BACKGROUND OF THE INVENTION

Genetic diseases are due, in particular, to dysfunction in the expression of specific genes or to the expression of non-functional mutated polypeptides. Cystic fibrosis, for example, is regarded as the most frequently occurring of the lethal genetic diseases (1/2000) with a mean life expectancy of from 25 to 30 years, and is characterized by substantial thickening of the secretions derived from the mucous membranes, by chronic pulmonary attacks and by insufficiency of the exocrine pancreas. Said disease is associated with disturbances in the transport of electrolytes, in particular chloride, across the epithelial membrane, which disturbances are the consequence of mutations in the CFTR (cystic fibrosis transmembrane conductance regulator) gene (Rommens, Science 245 (1989), 1059–1066; Rosenfeld, Chest 109 (1996), 241–252). The therapeutic solution which appears to be most suitable for this type of disorder is that of transferring the gene encoding a functional CFTR polypeptide into the target cells in order to correct the observed cellular dysfunction. Within the context of this approach, also termed gene therapy, several authors indicate that the cells of the respiratory epithelium are a target of choice, especially as a result of its accessibility, in particular by means of intrapulmonary delivery, for example by instillation into the lungs. It has been shown that a level of expression of approximately 5 to 7% of that of the normal CFTR gene has to be obtained in the target cells for restoration of the electrolyte transport to be observed. Similarly, several publications describe the possibility of eliminating tumours or, failing that, of delaying their progress, by using the technique of transferring genes into the cancerous target cells. Several approaches have been considered, in particular transferring immunostimulatory genes (immunotherapy) which are able to induce or activate a cell-mediated immune response against the tumour; as examples of the therapeutic uses of such genes, mention may be made of the administration of genes which encode cytokines; transferring cytotoxic genes which confer toxicity on cells which express them, for example the tk gene of type 1 herpes simplex virus (HSV-1); or transferring antioncogenes, that is tumour suppressor genes, such as the retinoblastoma gene or the p53 gene, or polynucleotides which are able to inhibit the activity of an oncogene, such as antisense molecules or ribozymes which are able to degrade the specific messenger RNAs of the oncogenes.

Over the course of the last 30 years, a large number of tools have been developed for introducing various heterologous genes into cells, in particular mammalian cells. These different techniques can be divided into two categories. The first category relates to physical techniques such as microinjection, electroporation or particle bombardment which, although effective, are to a large extent limited to in vitro applications, the implementation of which is cumbersome and delicate. The second category involves techniques relating to molecular and cell biology, where the gene to be transferred is combined with a biological or synthetic vector which promotes the introduction of the said material.

The vectors which are currently most effective are viral vectors, in particular adenoviral or retroviral vectors. The techniques which have been developed are based on the natural properties which these viruses possess for traversing cell membranes, evading degradation of their genetic material and enabling their genome to penetrate into the nucleus. These viruses have already been the subject of a large number of studies, and some of them are already employed experimentally as gene vectors in man with a view, for example, to vaccination, immunotherapy or therapy which is aimed at compensating for a genetic deficiency. Nevertheless, this viral approach suffers from a large number of limitations, in particular on account of the restricted cloning capacity within the viral genome, of the risks of infectious viral particles which have been produced being disseminated in the host organism and in the environment, of the risk of artefactual mutagenesis resulting from insertion in the host cell, in the case of retroviral vectors, and of the fact that immune and inflammatory responses are powerfully induced in vivo during therapeutic treatment, thereby substantially limiting the number of administrations which can be envisaged (McCoy, Human Gene Therapy 6 (1995), 1553–1560; Yang, Immunity 1 (1996), 433–442). These many drawbacks, in particular within the context of using viral vectors in man, have led several groups to develop alternative systems for transferring polynucleotides.

Several non-viral methods are available at the present time. Mention may be made, for example, of coprecipitation with calcium phosphate, use of cationic lipids such as DOTMA (Feigner, PNAS 84 (1987), 7413–7417), DOGS or Transfectam (Behr, PNAS 86 (1989), 6982–6986), DMRIE and DORIE (Felgner, Methods 5 (1993), 67–75), DC-CHOL (Gao, BBRC 179 (1991), 280–285), DOTAP (McLachlan, Gene Therapy 2 (1995), 674–622) or Lipofectamine; the use of receptors which mimic viral systems (for a review, see Cotten, Current Opinion in Biotechnology 4 (1993), 705–710); and the use of polymers such as polyamidoamine (Haensler, Bioconjugate Chem. 4 (1993), 372–379). However, although promising, these techniques suffer from a number of limitations, in particular their low level of in vivo efficacy, which substantially limits their application within the, context of a gene therapy. Furthermore, some of these techniques are either limited to in vitro applications, in particular on account of the toxic character of the molecule employed (polybrene may be mentioned as an example), or on account of inflammatory reactions in response to the introduction of these compounds (in the case of cationic lipids, for example; Scheule, Human Gene Therapy 8 (1997), 689–707), or are difficult to control, as in the case of receptors where a large quantity of the nucleic material is trapped in vesicles during endocytosis and is not therefore any longer available for the therapy. Finally, these techniques are relatively sensitive to environmental factors and long and delicate development is required in order to adapt them to the target cells or to the chosen mode of administration and, more particularly, in order to transfer them from the in vitro model to an in vivo application.

Wolff (Science 2478 (1990), 1465–1468) have described an attractive and simple system for introducing a polynucleotide into muscle cells, which system consists simply in injecting the purified polynucleotide, which is not associated with any other compound facilitating its introduction into the target cells, by the intramuscular route. The results which have more recently been obtained by means of intratracheal injection (Meyer, Gene Therapy 2 (1995), 450–460) or by means of injection into the arteries (Riessen, Human Gene Therapy 4 (1993), 749–758) confirm the interest which such a system affords. Nevertheless, the levels at which the genes which have been introduced into the tissues are expressed are still too limited to enable this technique to be implemented within the context of an efficient gene therapy, in particular in association with pulmonary disorders. Some studies suggest alternative methods in order to improve the introduction of this type of polynucleotide into cells. For example, the patent application WO95/26718 relates to methods of introducing genetic material into cells comprising the steps of contacting said cells with a genetic vaccine facilitator agent and a nucleic acid molecule. According to a specific embodiment described therein, the said genetic vaccine facilitator agent can consist in DMSO. Nevertheless, no experimental data is provided in said patent application and experiments conducted by Aubin (Somatic Cell Mol. Genet. 14 (1988), 155–167) or Rhim (Oncogene 4 (1989), 1403–1409) have underscored the necessity of combining the use of DMSO with the use of electrostatic bridging molecules such as polybrene. More specifically, Aubin describes a two-step process. According to a first, obligatory step, the DNA to be transfected is brought into contact with an electrostatic bridging molecule, i.e. polybrene, in order to enable this DNA to adsorb to the cell surface, and, according to a second step, the DNA which has thus been adsorbed is brought into contact with DMSO in order to improve the introduction of the DNA into the cells. These studies do not make it possible to specify a protocol which is suitable for an in vivo application, which is intended to introduce a polynucleotide, more specifically a polynucleotide which is free of any transfection-facilitating compounds, effectively into different cell types, and which improves the level at which the said nucleic acid is expressed in the said target cells. Besides this, Oudhiri (PNAS 94 (1997), 1651–1656) demonstrated that no expression of the luciferase gene was obtained in pulmonary cells following the intratracheal injection of a plasmid which was free of any compound which facilitated its introduction into cells.

BRIEF SUMMARY OF THE INVENTION

Thus, the technical problem underlying the present invention is to provide means and methods for effectively transferring therapeutically active substances into a target cell.

The solution to this technical problem is achieved by the embodiments characterized in the claims, namely the applicant has now developed a specific composition for transferring a therapeutically active substance, preferably a polynucleotide, into the interior of a target cell, which composition can be envisaged for use, in particular, in vivo within the context of gene therapy, in particular on account of the harmlessness of its components.

Thus, the present invention relates, first of all, to a composition, characterized in that it comprises a mixture of at least one therapeutically active substance and at least one polar compound which is selected from among a specific group of aprotic polar compounds.

DETAILED DESCRIPTION OF THE PREFERRED EMBODIMENTS OF THE INVENTION

In accordance with the present invention, "aprotic polar compound" is understood as referring to a compound which does not contain any positively polarised hydrogen atoms (aprotic). The properties of such compounds are widely described in the literature (see, for example, Vollhardt and Schore, 1994, Traité de Chimie Organique [Treatise on Organic Chemistry], 2nd edition, Ed. De Boeck University). Such compounds can, in particular, be obtained naturally or synthetically, or by the chemical modification of a first compound which does not initially exhibit the abovementioned properties. The skilled person is in possession of the necessary knowledge to identify such compounds. The aprotic polar compounds to be employed in the compositions, methods and uses of the present invention such as those described below may be obtained from various commercial sources or produced as described in the prior art. A large number of polar compounds can be considered for use within the context of the invention.

According to a first aspect of the present invention, preference is given to mentioning the aprotic polar compounds as defined by:

(a) formula I:

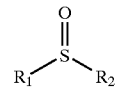

wherein R1 and R2 are identical or different and are aryl, alkyl, cycloalkyl, fluoroalkyl, alkenyl or oxyalkyl radicals of 1 to 8 carbon atoms which are optionally repeated, which are linear or branched and which are optionally substitued,
with the proviso that when R1 or R2 is a radical of 1 or 2 carbon atoms, R2 or R1, respectively, is a radical of at least 3 carbon atoms, with it being possible for R1 and R2 to be linked in order to cyclize the molecule;

(b) formula II:

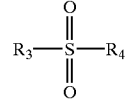

wherein R3 and R4 are identical or different and are aryl, alkyl, cycloalkyl, fluoroalkyl, alkenyl or oxyalkyl radicals of 1 to 8 carbon atoms which are optionally repeated, which are linear or branched and which are optionally substituted, with it being possible for R3 and R4 to be linked in order to cyclize the molecule;

(c) formula III:

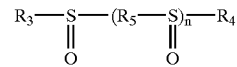

wherein R3 and R4 are identical or different and are aryl, alkyl, cycloalkyl, fluoroalkyl, alkenyl or oxyalkyl radicals of 1 to 8 carbon atoms which are optionally repeated, which are linear or branched and which are optionally substituted,
R5 is $(CH_2)x$, independently of one another in each $[R5-S]_n$ repeat, where x=1 to 6, with R5 being optionally substituted,
n=1 to 50
with it being possible for R3 and R4 to be linked in order to cyclize the molecule; or (d) dimethylformamide, dimethylacetamide, tetramethylurea or a derivative of any one thereof.

Preferably, said radicals of R1, R2, R3 and/or R4 comprise 2 to 6 carbon atoms, more preferably 2 to 4 carbon atoms, and particularly preferred 2 or 3 carbon atoms.

The expression "alkenyl" is understood as meaning that the carbon chain can include one or more double bond(s) along the said chain.

According to the invention, the R1, R2, R3, R4 and/or R5 groups of the polar compounds can be substituted. Such substitutions can, in particular, consist of a labelling molecule (see labelling molecules in U.S. Pat. No. 4,711,955) enabling, for example, visualization of the distribution of the compounds, or of complexes incorporating them, after in vitro or in vivo administration; a cell targeting molecule (ligand) or an anchoring molecule. These elements, which have been widely described in scientific publications, allow targeting of a specific cell type, facilitating penetration into the cell, lysis of endosomes or even intracellular transport towards the nucleus. These elements may be composed of all or part of sugars, glycol, peptides (e.g. GRP, Gastrin Releasing Peptide), oligonucleotides, lipids, hormones, vitamins, antigens, antibodies (or fragments thereof), specific membrane receptor ligands, ligands capable of reaction with an anti-ligand, fusogen peptides, nuclear localization peptides, or a combination of said compounds, e.g. galactosyl residues to target the asialoglycoprotein receptor on the surface of hepatocytes, the INF-7 fusogen peptide derived from the HA-2 subunit of the influenza virus hemagglutinin (Plank, J. Biol. Chem. 269 (1994), 12918–12924) for membrane fusion, or a nuclear signal sequence derived from the T-antigen of the SV40 virus (Lanford, Cell 37 (1984), 801–813) or from the EBNA-1 protein of the Epstein Barr virus (Ambinder, J. Virol. 65 (1991), 1466–1478).

According to the invention, the said aprotic polar compound is, in particular, selected from the group consisting of di-n-propyl sulphoxide (DPSO), dimethyl sulphone, sulpholane, tetramethylene sulfoxide (TEMSO), 1-methyl-2-pyrrolidone, methyl-di-methylsulfoxide, methyl-di-ethylsulfoxide and their derivatives. According to an advantageous form of the invention, the said aprotic polar compound is selected from the group consisting of di-n-propyl sulphoxide (DPSO) and its derivatives. As described in the appended examples DPSO was found to significantly facilitating the uptake of DNA by cells when administered in admixture with the DNA. Enantiomer forms of said molecules are also included in the scope of the present invention.

For the purpose of the present invention "derivative" of any of the aforementioned compounds means molecules the chemical structure of which is based on that of the above described compounds and which can be used for transferring a substance into a target cell. The capability of facilitating the uptake of a substance by cells during transfection of said substance with the thus derived compounds may even be enhanced as compared to the natural occurring aprotic polar compounds and those mentioned above. Methods for the preparation of such derivatives are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Said derivatives can be tested for transfection utility according to methods known in the art or as described, for example, in the appended examples. Furthermore, computer aided design of appropriate derivatives and analogues can be used, for example, according to methods known in the art. Furthermore, a three-dimensional and/or crystallographic structure of DPSO and other related aprotic polar compounds can be used for the design of compounds capable of facilitating DNA uptake (Rose, Biochemistry 35 (1996), 12933–12944; Rutenber, Bioorg. Med. Chem. 4 (1996), 1545–1558).

According to another embodiment of the invention, the said aprotic polar compound is selected from the group consisting of dimethylformamide (DMF), dimethylacetamide, tetramethylurea (TMU) and their derivatives.

The active substance of the composition of the present invention includes, but is not limited to peptides, proteins, polynucleotides, antibodies, small organic compounds ligands, hormones, peptidomimetics, PNAs and the like preferably capable of inducing and/or mediating a physiological response in a subject. Preferably, the active substance of the composition according to the invention is a polynucleotide, with the aprotic polar compound then making it possible to improve the ability of the polynucleotide to be transfected into a cell.

"Polynucleotide" is understood as meaning a naturally isolated or synthetic, linear or circular, double-stranded or single-stranded DNA and/or RNA fragment, with the term designating a precise sequence of labelled or unlabelled (see, for example, U.S. Pat. No. 4,711,955 or EP 302175), modified or unmodified (see, by way of example, U.S. Pat. No. 5,525,711) nucleotides and making it possible to define a fragment or a region of a nucleic acid without limiting its size. Polynucleotide is understood as referring, in particular, to a cDNA; to a genomic DNA; to a plasmid DNA; to a polynucleotide which is free of any compound which facilitates its introduction into cells; to a polynucleotide which is associated with at least one polypeptide, in particular a polypeptide of viral origin, more particularly of adenoviral or retroviral origin, or with a synthetic polypeptide; to a polynucleotide which is associated with a ligand; to a polynucleotide which is associated with at least one cationic amphiphile, in particular lipids; to a polynucleotide which is associated with at least one cationic or neutral polymer; to a messenger RNA; to an antisense RNA; to a ribozyme; to a transfer RNA; to a ribosomal RNA; or to a DNA which encodes such RNAs.

According to one particular embodiment of the invention, the said polynucleotide comprises a gene of interest and elements which enable the said gene of interest to be expressed. In this embodiment, the said polynucleotide is advantageously in plasmid form. The elements which enable expression to take place are the totality of the elements which enable the said DNA fragment to be transcribed into RNA (antisense RNA or mRNA) and the mRNA to be translated into polypeptide. These elements are, in particular, promoter sequences and/or regulatory sequences which are effective in the said cell and, where appropriate, the sequences which are required for enabling the said polypeptide to be secreted or expressed at the surface of the target cells. By way of example, mention may be made of the promoters of the RSV, MPSV, SV40, CMV or 7.5 k viruses, or of vaccinia virus, or the promoters of the genes which encode muscle creatine kinase, actin and pulmonary surfactant. It is furthermore possible to select a promoter sequence which is specific for a given cell type or which can be activated under defined conditions. The literature provides a great deal of information relating to such promoter sequences. Furthermore, the said polynucleotide can include at least two identical or different sequences exhibiting transcriptional promoter activity and/or at least two identical or different DNA coding sequences which are located contiguously or at a distance, and in the same direction or in the opposite direction, with respect to each other without the function of the transcriptional promoter or the transcription of the said sequences being affected thereby. Similarly, it is possible, in this type of nucleic acid construct, to introduce "neutral" nucleic acid sequences or introns which do not affect transcription and which are spliced before the translation stage. Sequences of this nature, and their uses, are described in the literature. The said polynucleotide can also encompass sequences which are required for intracellular transport, for replication and/or for integration. Such sequences are well known to the skilled person. In addition, the polynucleotides according to the present invention can also be polynucleotides which are modified such that they are unable to integrate into the genome of the target cell, or polynucleotides which are stabilized with agents such as, for example, spermine.

The composition of the invention may further comprise a selectable marker gene, either linked to the above described polynucleotides or as separate nucleic acid molecules, e.g. in a recombinant plasmid. This embodiment is particularly suited for ex vivo treatment of tissue, cells and organs. Following the introduction of foreign DNA, engineered cells may be allowed to grow for 1–2 days in an enriched media, and then are switched to a selective media. The selectable marker in the recombinant plasmid confers resistance to the selection and allows for the selection of cells having stably integrated the plasmid into their chromosomes and grow to form foci which in turn can be cloned and expanded into cell lines. A number of selection systems may be used, including but not limited to the herpes simplex virus thymidine kinase (Wigler, Cell 11 (1977), 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) in tk$^-$, hgprt$^-$ or aprt$^-$ cells, respectively. Also, antimetabolite resistance can be used as the basis of selection for dhfr, which confers resistance to methotrexate (Wigler, Proc. Natl. Acad. Sci. USA 77 (1980), 3567; O'Hare, Proc. Natl. Acad. Sci. USA 78 (1981), 1527), gpt, which confers resistance to mycophenolic acid (Mulligan, Proc. Natl. Acad. Sci. USA 78 (1981), 2072); neo, which confers resistance to the aminoglycoside G-418 (Colberre-Garapin, J. Mol. Biol. 150 (1981), 1); hygro, which confers resistance to hygromycin (Santerre, Gene 30 (1984), 147); or puromycin (pat, puromycin N-acetyl transferase). Additional selectable genes have been described, for example, trpB, which allows cells to utilize indole in place of tryptophan; hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.).

Suitable vectors and plasmids useful to be employed in the composition of the invention for in vitro or in vivo gene therapy are described in the literature and are known to the person skilled in the art; see, e.g., Giordano, Nature Medicine 2 (1996), 534–539; Schaper, Circ. Res. 79 (1996), 911–919; Anderson, Science 256 (1992), 808–813; Isner, Lancet 348 (1996), 370–374; Muhlhauser, Circ. Res. 77 (1995), 1077–1086; Wang, Nature Medicine 2 (1996), 714–716; WO94/29469; WO 97/00957 or Schaper, Current Opinion in Biotechnology 7 (1996), 635–640, and references cited therein. Preferably, said vector is a gene transfer or targeting vector. Methods which are well known to those skilled in the art can be used to construct the above mentioned polynucleotides, plasmids and recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989).

Within the context of the present invention, the polynucleotide can be homologous or heterologous to the target cell. It can be advantageous to use a polynucleotide which encodes all or part of a polypeptide, in particular a polypeptide which exhibits a therapeutic or prophylactic activity, more specifically an immunogenic activity of the cellular or humoral type. The term polypeptide is to be understood as being without restriction with regard to the size of the polypeptide or the degree to which it is modified (for example by glycosylation). By way of example, mention may be made of the genes which encode an enzyme, a hormone, a cytokine, a membrane receptor, a structural polypeptide, a polypeptide which forms a membrane channel, a transport polypeptide, an adhesion molecule, a ligand, a factor for regulating transcription, translation, replication or transcript stabilization, or an antibody, such as, for example, the gene which encodes the CFTR protein, dystrophin, factor VIII or factor IX, HPV E6/E7, MUC1, BRAC1, interferon, the interleukins (IL-2, IL4, IL-6, IL-7 and IL-12), tumour necrosis factor (TNF) alpha or GM-CSF (granulocyte macrophage colony stimulating factor), or the tk gene of herpes simplex virus type 1 (HSV-1), the retinoblastoma gene or the gene for p53, or all or part of immunoglobulins, such as the $F(ab)_2$, Fab' and Fab fragments, or the anti-idiotype immunoglobulins (U.S. Pat. No. 4,699,880). It will, of course, be understood that this list is not limiting and that other genes can be employed.

According to the present invention, it may be desirable to obtain a composition which comprises the highest possible concentration of polynucleotide in order to be able, if necessary, to administer the smallest possible volume of composition according to the invention. The skilled person is in possession of adequate knowledge to enable him to adjust this concentration in accordance with the solubilizing power of the medium in which the said polynucleotide is dissolved. According to a preferred embodiment, the said aprotic polar compound is in aqueous solution, that is to say it is diluted in an aqueous solution which is, where appropriate, saline and buffered. The skilled person is in possession of sufficient knowledge to enable him to select the aqueous solution which is most appropriate for the targeted cell type. More specifically, the said polar compound is in solution in water or in a buffer, for example 20 mM Hepes, pH 7.5. The volume of the aprotic polar compound can represent from 0.1 to 100% of the total volume of the composition, more especially from 5 to 50%, advantageously from 15 to 20%.

The present invention further relates to a pharmaceutical composition comprising any one of the aformentioned compositions of the invention and optionally a pharmaceutically acceptable carrier or exipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intratracheal, intrapulmonary, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular substance to be administered, sex, time and route of administration, general health, and other drugs being administered concurrently. Generally, the regimen as a regular administration of the pharmaceutical composition should be in the range of 1 µg to 10 mg as the bioactive compound per day. If the regimen is a continuous infusion, it should also be in the range of 1 µg to 10 mg as the bioactive compound per kilogram of body weight per minute, respectively. Progress can be monitored by periodic assessment. Dosages will vary but a preferred dosage for intravenous administration of polynucleotides, e.g., DNA is from approximately $10^6$ to $10^{16}$ copies of the DNA molecule. The compositions of the invention may be administered locally or systemically. Administration will generally be parenterally, e.g., intravenously; DNA may also be administered directly to the target site, e.g., by catheter to a site in an artery. Furthermore, the compositions of the invention can be bound to microcapsules or microspheres before injection. One may either use an in vivo gene-transfer approach for which multiple devices, like double balloon or other catheters have been designed or via direct injection into the targeted tissue as described above. Alternatively it is possible to use an ex vivo approach isolating cells which are known to lodge in tissues from the body which are then transfected using one of the above mentioned compositions and reinjected.

In a still further embodiment, the present invention relates to a vaccine comprising any one of the aforementioned compositons. In this embodiment the therapeutically active substance is preferably an antigen or a polynucleotide encoding the same capable of generating a protective immunological response to a disease in a human or an animal susceptible to such disease. The vaccines of the present invention can be prepared according to methods well-known in the art. Immunogenicity of antigens used for vaccination can be enhanced, for example, programming either a Th1- or a Th2-directed immune response, e.g., by co-transducing cDNA coding for secreted cytokines or chemokines or membrane molecules. The vaccines can be, e.g., injected either intradermally, subcutaneously, intramuscularly or, particularly in case of anti-tumor vaccination, into areas of tumor growth or into lymphatic vessels or lymph nodes draining areas of tumor growth.

In another embodiment the present invention relates to a diagnostic composition comprising any one of the above described compositions of the invention and optionally suitable means for detection. In this embodiment, the therapeutically active substance is preferably labled. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. In addition or alternatively, the therapeutically active substance comprises a marker gene encoding a directly or indirectly detectable protein such as β-galactosidase, green fluorescent protein or luciferase; see also the appended examples. The diagnostic composition of the invention can advantageously be used for targeting, e.g., light emission to selected regions, as well as for tracking entities within the subject. In addition, animal models for disease states can be accomplished by using the above described compositions, as are methods for localizing and tracking the progression of disease or a pathogen within the animal, and for screening putative therapeutic compounds effective to inhibit the disease or pathogen. Methods for detecting and localizing light originating from a mammal are described in the prior art, e.g., WO 97/18841 and references cited therein.

The present invention also relates to the use of a composition according to the invention for transferring at least one therapeutically active substance, in particular a polynucleotide, into target cells in vitro, ex vivo or in vivo, more especially in vivo.

The introduction or transfer process is by itself well known. "transferring or transfer" means that the therapeutically active substance is transferred into the cell and is located, at the end of the process, inside said cell or within or on its membrane. If the active substance is a nucleic acid, this is called "transfection". Transfection can be verified by any appropriate method, for example by measuring the expression of said gene or by measuring the concentration of the expressed protein.

"Target cells" according to the invention are understood as meaning prokaryotic cells, yeast cells and eukaryotic cells, plant cells, human or animal cells and, in particular, mammalian cells. In addition, cancerous cells should also be mentioned. In vivo, the invention can be applied within the interstitial or luminal space of tissues such as the lung, the trachea, the skin, muscle, the brain, the liver, the heart, the spleen, bone marrow, the thymus, the bladder, lymph, blood, blood vessels, the pancreas, the stomach, the kidney, the ovaries, the testicles, the rectum, the peripheral or central nervous system, the eyes, the lymphatic organs, cartilage and endothelium. According to an advantageous choice of the invention, the target cell is a muscle cell, a haematopoietic stem cell or else an airways cell, more especially a tracheal or pulmonary cell, advantageously a respiratory epithelium cell.

The invention also relates to a process for transferring a therapeutically active substance into a target cell, according to which the said cell is brought into contact with a composition according to the invention. Advantageously, this process includes an additional step which consists of warming the composition before bringing it into contact with the cell.

It should also be understood that according to the present invention, the "composition" means that the therapeutically active substance and the polar compound included in it are associated or combined together in such a way that said active substance cannot be considered as free of facilating agent. For example, in the special case where said active substance is plasmid DNA, applicant has shown the physical properties of DNA are modified in the presence of DPSO. Therefore, a skilled person can readily envisage that this composition comprising said active substance and said polar compound can be obtained in vitro, but also in vivo, after separate administration of the said compounds to the target organ or tissue as far as the first compound remains available to form the claimed composition in situ following the later administration of the second compound. This independent mode of administration should be considered as an equivalent implementation of the present invention.

As mentioned above, the compositions according to the invention can be used as medicaments for diagnostic therapeutic, prophylactic or vaccination purposes. For this reason, the invention also relates to compositions of the invention as medicaments for therapeutic, prophylactic or vaccination purposes.

In particular, the compositions of the invention can be used for implementing a method of therapeutic treatment which consists in transferring at least one therapeutically active substance, in particular a polynucleotide, into target cells. Preferably, these target cells are mammalian cells. The mammalian cells are, in particular, lung cells, muscle cells or else haematopoietic stem cells.

A composition according to the invention may be administered by the intramuscular, intratracheal, intranasal, intracerebral, intrapleural, intratumoral, epidermal, intravenous or intraarterial route, using a syringe or any other equivalent means, including systems which are suited for treating airways or mucous membranes, such as inhalation, instillation or aerosolization. Mention may also be made of administration by means of applying a cream, by means of oral administration or by any other means which is perfectly well known to the skilled person and which can be applied to the present invention.

According to the present invention, and within the context of an in vivo gene therapy, it is possible to repeat the proposed procedure several times, in a given patient, without any significant immune reaction being triggered against one of the administered compounds. The administration can take place in one single dose or in doses which are repeated once or several times at particular intervals. The appropriate route of administration and dosage vary in accordance with a variety of parameters, for example the individual or the disease to be treated, or else the polynucleotide to be transferred.

The invention relates, more specifically, to the use of a composition according to the invention for preparing a medicament for diagnostic therapeutic, prophylactic or vaccination purposes, which medicament is intended for treating the human or animal body by means of gene therapy. According to a first possibility, the medicament can be administered directly in vivo (for example into a muscle, into the lungs using an aerosol, etc.). It is also possible to adopt the ex vivo approach, which approach consists in withdrawing cells from the patient (stem cells of the bone marrow, peripheral blood lymphocytes, muscle cells, etc.), transfecting them in vitro in accordance with the present invention and then readministering them to the patient.

Finally, the invention relates to a cell which is transfected with a composition as previously defined, in particular a prokaryotic cell, or a yeast or eukaryotic cell, in particular an animal cell, in particular a mammalian cell, more especially a cancerous cell. According to a preferred embodiment of the invention, the said cell is an airways cell, more especially a tracheal or pulmonary cell, advantageously a cell of the respiratory epithelium. In the case of airway delivery, prior administration of bronchodilator compounds (for example, theophylline) could be advantageous. The applicant has shown that oral administration of 0.3 mg of theophylline (Dilatrane) to the mice about 30 min before incubation of a composition comprising DPSO can result in a slightly increase of the expression level compared with administration without this pretreatment.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example, the public database "Medline" may be utilized and is available on Internet. Further databases and internet addresses, such as Infobiogen and the databases available on the National Institutes of Heath web site, are known to the person skilled in the art and can also be obtained using an internet search engine such as Lycos. An overview of patent information in biotechnology and a survey of relevant sources of patent information useful for retrospective searching and for current awareness in given in Berks, TIBTECH 12 (1994), 352–364.

The compositions, uses, methods of the invention can be used for the treatment of all kinds of diseases the treatment and/or diagnostic of which being related to or dependent on the transfer of therapeutic substances in cells. The pharmaceutical compositions, methods and uses of the present invention may be desirably employed in humans, although animal treatment is also encompassed by the methods and uses described herein.

The present invention is illustrated by the following examples 1 to 7 while referring to FIGS. 1 to 5.

A better understanding of the present invention and of its many advantages will be had from the following examples, given by way of illustration.

EXAMPLE 1

Preparation of Compositions in Which the Polar Compound is DESO or DPSO

Figure 1:
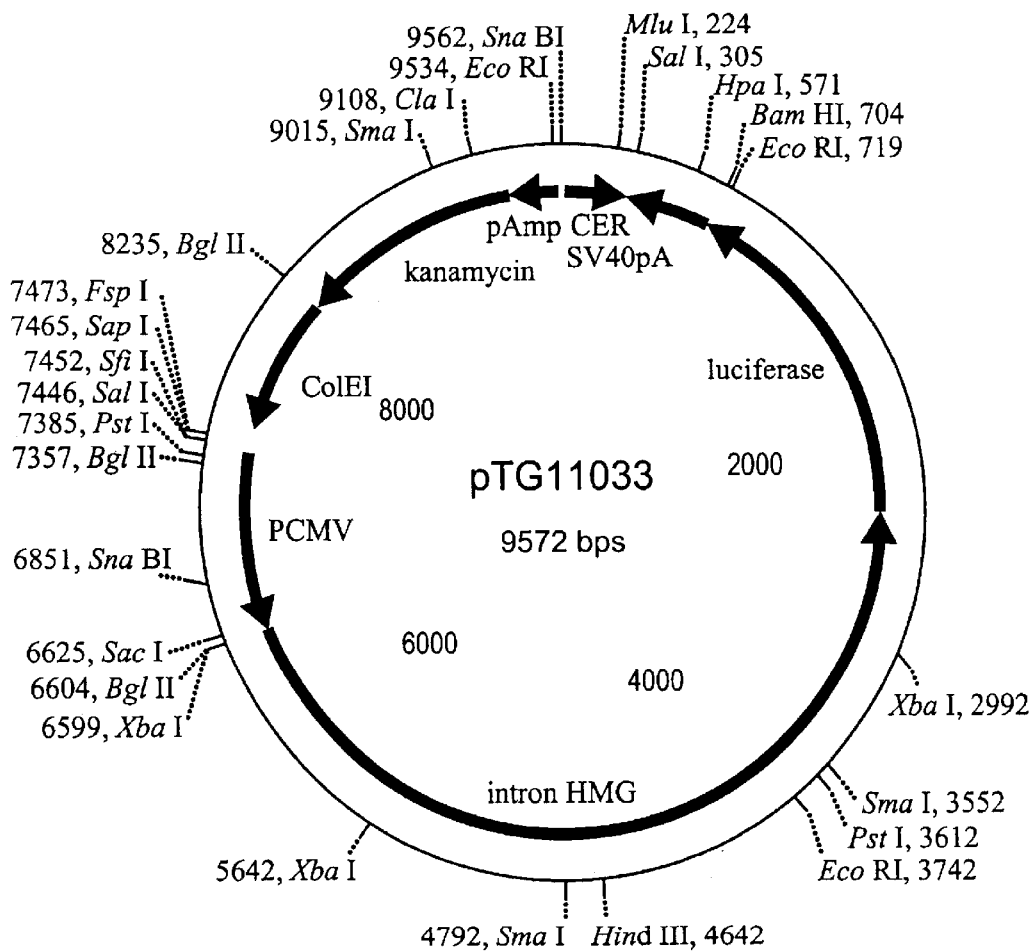
FIG. 1: Map of the plasmid pTG11033.

The chosen polynucleotide, i.e. the plasmid pTG11033 (FIG. 1), encompasses the gene encoding luciferase placed under the control of the CMV promoter, intron 1 of the HMG gene and the SV40 polyA termination signal. The plasmid DNA contained in 250 μl of a 1 mg/ml solution of purified plasmid (purified by centrifugation in a cesium chloride gradient) is precipitated with ethanol. After having been centrifuged, washed with 70% ethanol and dried, the nucleic acid pellet is taken up in a given volume of DESO or DPSO and of 20 mM Hepes buffer, pH 7.5, in order to give the following compositions as shown in Table I below:

|  | 15% DESO (v/v) | 15% DPSO (v/v) |
| --- | --- | --- |
| 50 μg of DNA/50 μl | 37.5 μl of DESO, 20 mM Hepes, pH 7.5, QS for 250 μl | 37.5 μl of of DPSO, 20 mM Hepes, pH 7.5, QS for 250 μl |

EXAMPLE 2

Administration of the Compositions by Means of Intratracheal Injection

The 8-week-old female mice (B6/SJLF1, Iffa Credo) were anaesthetized by means of intraperitoneal injection (physiological saline, IMALGENE 1000, xylazine/ROMPUN). After the skin has been disinfected with 70% ethanol, an incision is made in order to expose the trachea, into which 50 µl of the compositions of Example 1 can be injected using a syringe. Each composition is injected into at least three different mice. The expression levels are compared with those obtained after injecting 50 µg of DNA in 50 µl of 20 mM Hepes, pH 7.5, without any addition of polar compound. A control in which the mice are not injected is also included in the protocol.

EXAMPLE 3

Measuring the Luciferase Activity in the Tissues of the Injected Mice

The mice are sacrificed two days after the injections. The lungs and the trachea are treated independently. The tissues are frozen in liquid nitrogen and stored at −80° C. In order to measure the luciferase activity, the tissues are ground up mechanically using a pestle in a mortar which is placed on dry ice. 500 µl or 200 µl of a lysis buffer (Promega) are added to the tissue fragments obtained from the lungs or the trachea, respectively, and the solution is subjected to three steps of freezing/thawing. The cell debris is removed by centrifugation and the luciferase activity (in RLU/min, relative light unit per minute) is measured on 20 µl of supernatant, in accordance with the supplier's (Promega) instructions, by adding 100 µl of reagent and measuring the activity by means of luminescence. The luciferase activity which is measured is standardized in relation to the quantity of protein with the aid of a standard scale which is generated using commercially available luciferase (Promega). The quantity of total protein is also determined by means of the bicinchoninic acid (BCA) colorimetric method (Smith, Anal. Biochem. 150 (1985), 76–85) using an aliquot of supernatant. This makes it possible to express the luciferase activity in RLU per milligram of protein extracted from the tissues. For a given composition, the activity under consideration corresponds to the mean of the values obtained from the three injected mice.

EXAMPLE 4

Results Obtained

Figure 2:
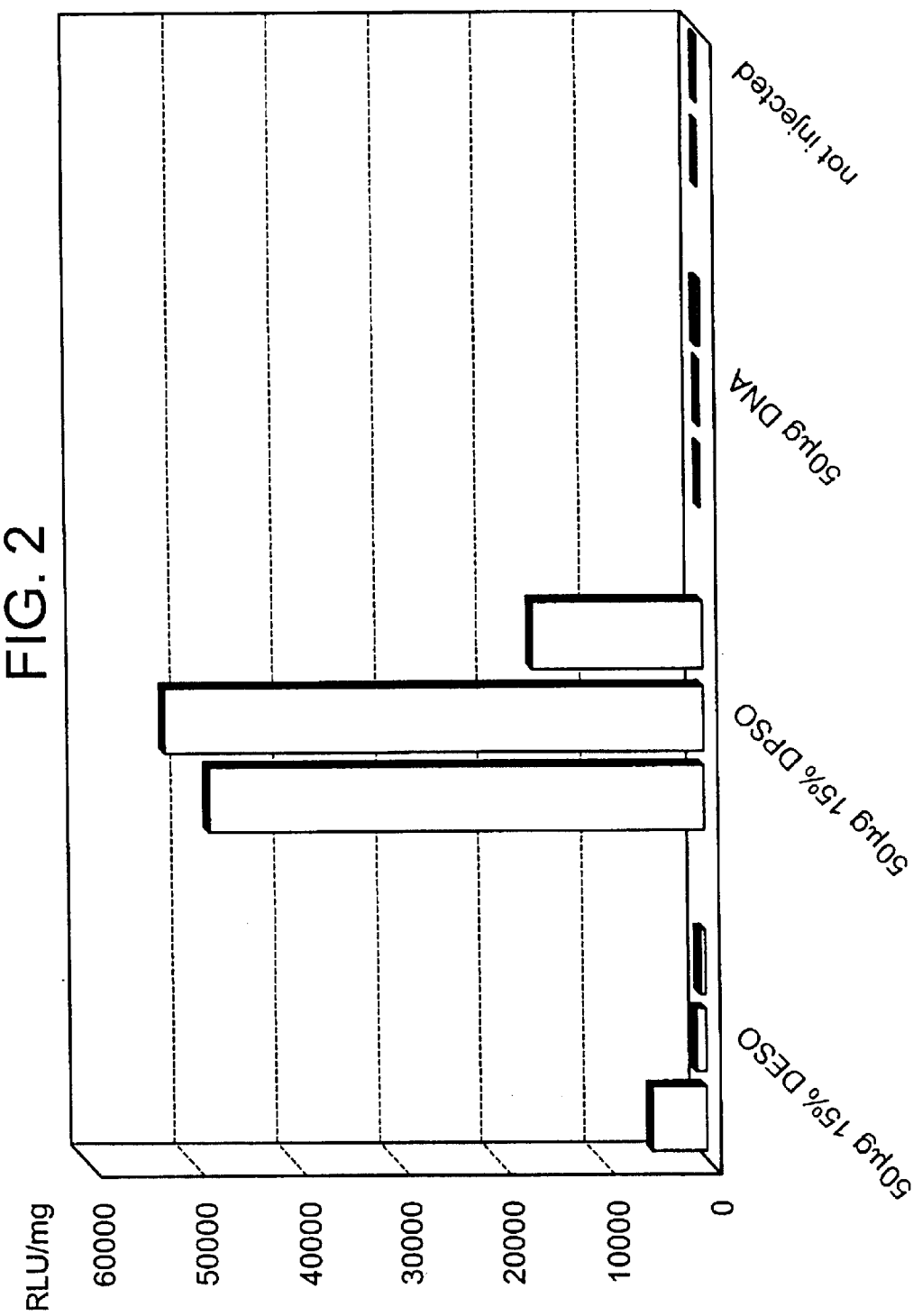
FIG. 2: Levels at which the gene encoding luciferase was expressed (RLU/mg of protein) in the lungs following injection of a composition comprising 50 μg of DNA and 15% (v/v) of DESO or DPSO in a 20 mM Hepes buffer, pH 7.5.
Figure 4:
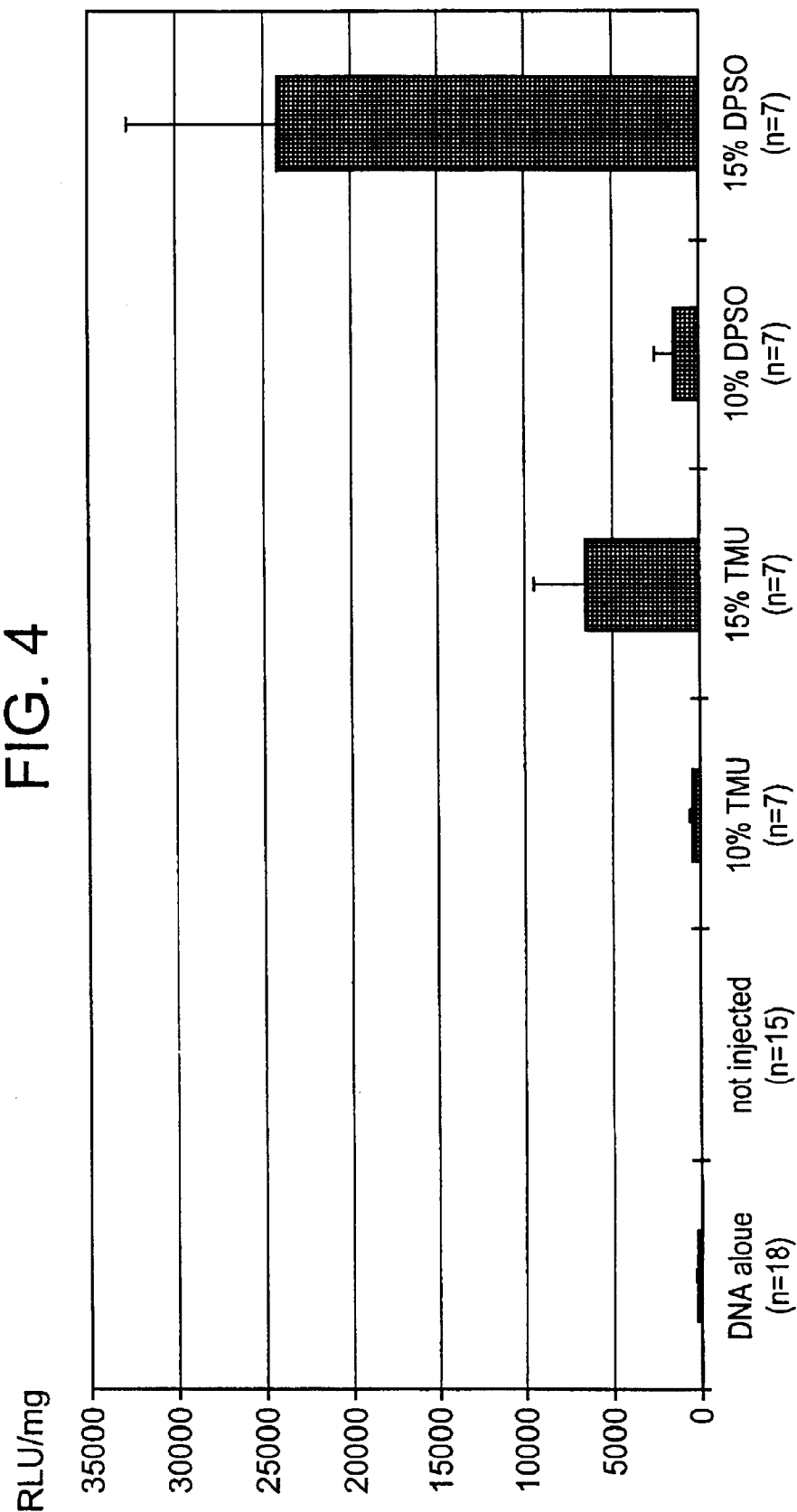
FIG. 4: Levels at which the gene encoding luciferase was expressed (RLU/mg of protein) in lungs following the injection of a composition comprising 50 μg of DNA and, where appropriate, 10 or 15% (v/v) of TMU or DPSO in a 20 mM Hepes buffer, pH 7.5. The values shown are in each case calculated from the mean of the results observed in n mice injected with the same composition. SEM: standard error of the mean (see: Burke, Scientific data management 9 (1997), 32–38).

The results obtained from the extracts derived from the lungs are shown graphically in FIGS. 2 and 4. These results demonstrate that while no expression of the luciferase gene is observed in the pulmonary tissues when the polynucleotide is injected on its own (50 µg), the addition of DPSO to the injected composition increases expression.

These results demonstrate that DPSO on its own is an effective compound for improving the ability of a polynucleotide to be transfected into a cell after the said compositions have been injected intratracheally, with the level of expression being markedly improved as compared with injection of the polynucleotide alone.

EXAMPLE 5

Other Aprotic Polar Compounds Which Were Tested

In an identical manner, we demonstrated that it was possible to employ other aprotic polar compounds in accordance with the present invention. In order to do this, various compositions were prepared in accordance with the protocols described in Examples 1 and 4. These compositions more specifically comprise: 50 µg of plasmid pTG11033/50 µl and a variable percentage (10 or 15%) of a substance selected from: DPSO, tetramethylene sulfoxide (TEMSO), (see Johnson and Keiser, 1973, Organic Synthesis Coll. 5 (1973), 791), DMSO, tetramethylurea or sulpholane. Each of the resulting compositions was then injected intratracheally into 8 to 12-week-old mice (C57BL/6, Iffa Credo) using the protocol which was previously described in Example 2.

Figure 3:
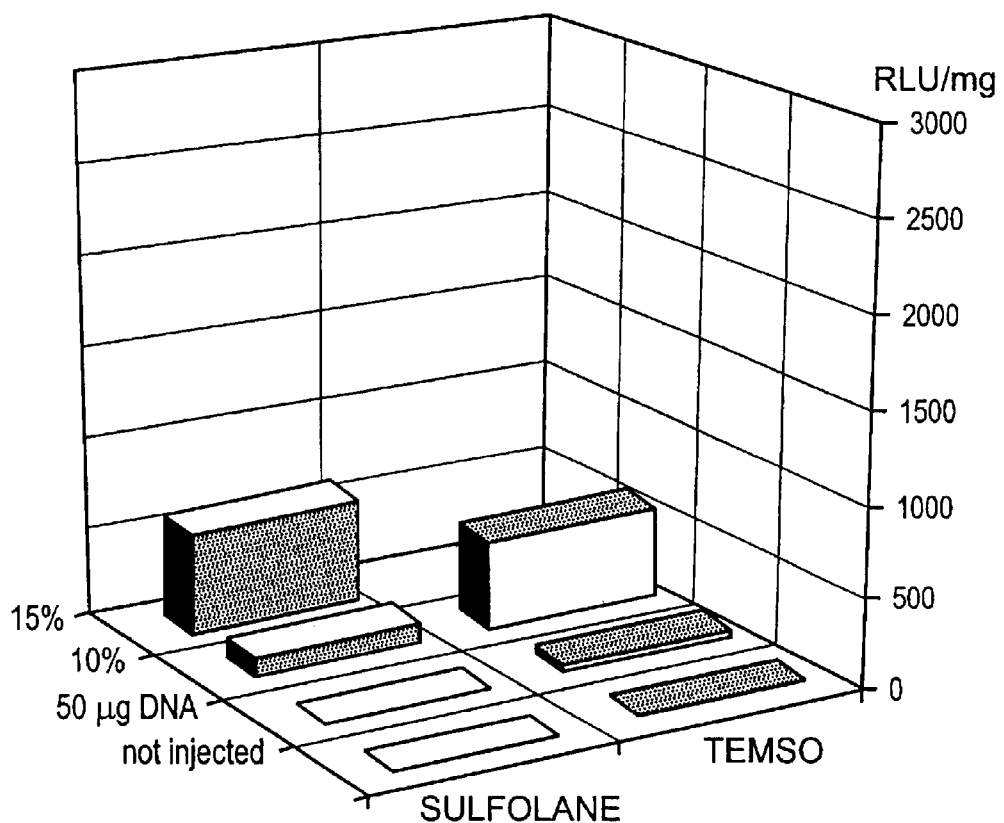
FIG. 3: Levels at which the gene encoding luciferase was expressed (RLU/mg of protein) in the lungs following the injection of a composition comprising 50 μg of DNA and, where appropriate, 10 or 15% (v/v) of different polar compounds in a 20 mM Hepes buffer, pH 7.5. The values shown are in each case calculated from the mean of the results which are observed in mice injected with the same composition.

The results which were obtained, FIGS. 3 and 4, demonstrate that the invention can be implemented by using various aprotic polar compounds. Thus, the different compositions tested, which compositions comprise a polynucleotide and a aprotic polar compound such as those listed above, make it possible to obtain a markedly improved transfection of the pulmonary cells, following intratracheal injection, as compared with when the polynucleotide is injected on its own under conditions which are identical, particularly as regards concentration.

The best results are observed with the compositions which comprise DPSO or TMU. In the case of each of these polar compounds, it was also shown that, for the quantity of DNA tested (50 µg), it was possible to improve the measured level of expression of the luciferase-encoding gene (FIG. 4) by increasing the percentage of the said compound.

EXAMPLE 7

Recording of Plasmid DNA Melting Curves

Figure 5:
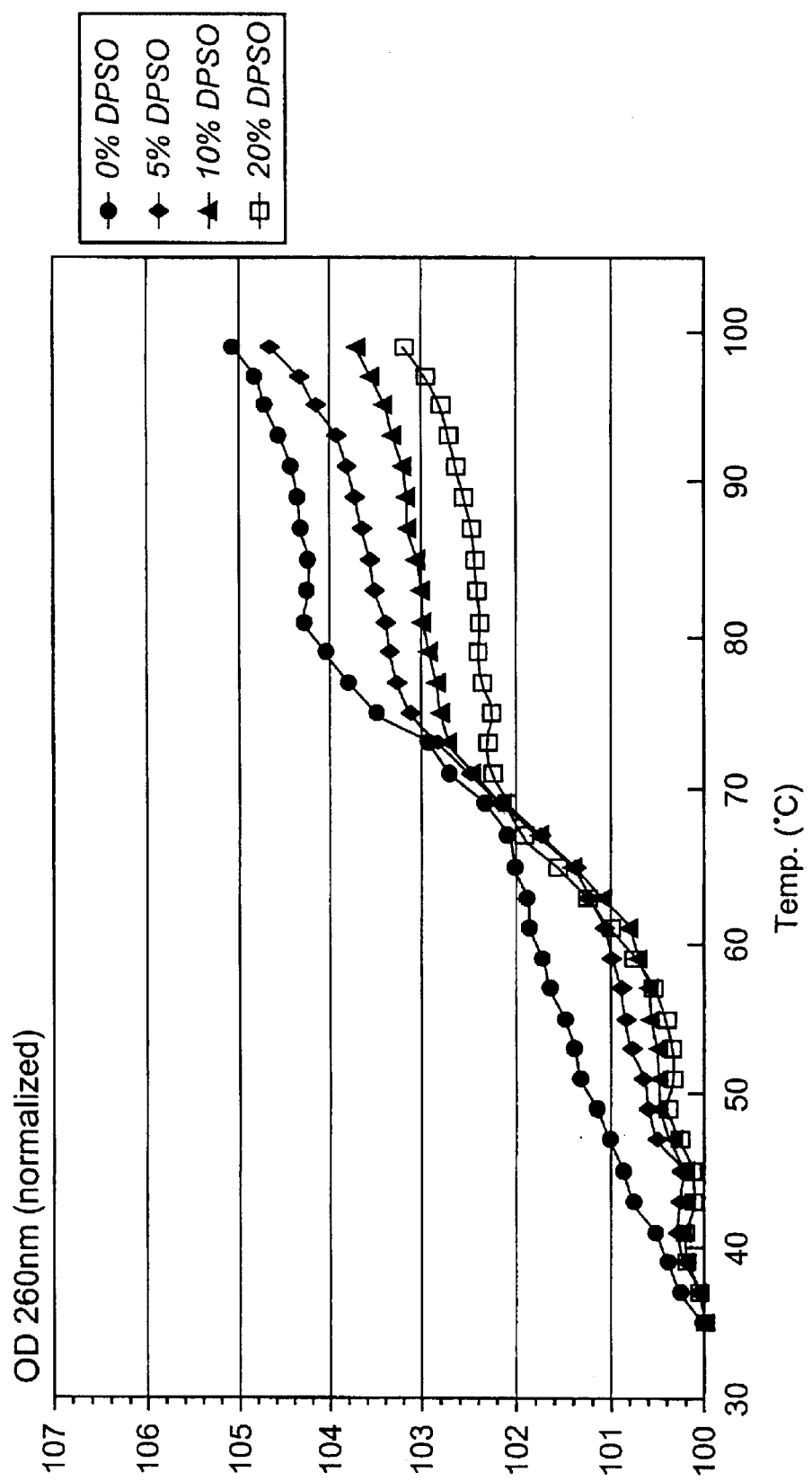
FIG. 5: PLASMID DNA MELTING CURVES +/− DPSO. 50 μg/ml plasmid DNA (pTG11033) in 20 mM HEPES, pH 7.5, or in 20 mM HEPES, pH 7.5, containing 5, 10, 15 or 20% DPSO were subjected to heating (4° C./min). Absorbance change was recorded and normalized to the starting absorbance at 35° C.

Plasmid DNA melting curves were recorded on a thermostated UV/Visible CARY/VARIAN spectrophotometer (sofware version: 3.04) using 2 quartz cuvettes (L=1cm) with Teflon stopper. Total volume of the sample: 1 ml (50 µg/ml plasmid DNA (pTG11033) in 20 mM HEPES, pH 7.5 with different percentages (0, 5, 10, 15, 20%) of di-n-propyl-sulfoxide (DPSO). The temperature gradient was 4° C./min and carried out from 35° C. to 100° C. at 260 nm (scale: 0.9–1.2 OD; 50 µg~1 OD). It would be shown (FIG. 5) that upon DNA melting curve assays, DNA alone ("naked" DNA) or DNA in the presence of DPSO ("solvoplexes") behaves differently: Absorbance change is lowered and occurs at higher temperature in the presence of sulfoxide compound. This can be interpreted as a DNA stabilizing effect of the DPSO (it takes a higher temperature to dissociate the DNA double strand).

EXAMPLE 8

Aerosolisation of Liposolvoplexes

The ultimate way of delivering vectors to the respiratory epithelium will be in the form of an aerosol. But DNA alone is rapidly degraded when aerosolized. This effect could be avoided by complexing the DNA as lipoplexes (DNA associated with a cationic amphiphile such as those described in patent application n° FR 97/15805, for example pTG90). It has been previously observed that lipoplexes alone gave only low or no expression in lung. In accordance with the present invention it was tested to combine the favorable characteristics of solvoplexes (complexes of the present invention) and lipoplexes. For this purpose, liposolvoplexes (DNA together with cationic lipids and DPSO) were prepared, aerosolised, collected in a cold trap and then injected intratracheally into mice. Lipoplexes with pTG90/DOPE alone did not result in luciferase gene expression after intratracheal injection, however, in the presence of DPSO, expression was observed for pTG90/DOPE liposolvoplexes. In general, after aerosolisation, expression levels were lower for liposolvoplexes tested, but still 86% of the activity observed for the same complexes before aerosolisation could be recovered for pTG90/DOPE/DPSO liposolvoplexes.

EXAMPLE 9

Synthesis of Di-sulfoxides 9.1 Methyl-di-methylsulfoxide (bis(Methylsulfinyl)methane, BiMSuM) ($=CH_3—SO—CH_2—SO—CH_3$)

10.5 ml of $CH_3SOCH_2SCH_3$ (12.5 g, 100 mmoles; Aldrich 17.795) are diluted at room temperature in 125 ml methanol. The solution is stirred and kept at 0° C. Dropwise 21.4 g $NaIO_4$ (100 mmoles) in 280 ml water are added during 90 min. The reaction mixture is kept, under stirring, for 15 h at 0° C. The advancement of the reaction is controlled by thinlayer chromatography (TLC, solvent: $CH_2Cl_2/CH_3OH$ 95/5, detection by $I_2$, $KMnO_4$; $CH_3SOCH_2SCH_3$, Rf=0.9; $CH_3SOCH_2SOCH_3$, Rf=0.33). The reaction mixture is filtered over Celite, which is rinsed with 300 ml water, 200 ml $CH_2Cl_2$, then 200 ml methanol.

The enriched organic fractions are pooled, dried over $Na_2SO_4$, and evaporated.

The product is purified and fractions containing the two enantiomers are enriched by 3 passages over a silica column (ID 4 cm, 100 g silice in $CH_2Cl_2$) and elution with 550 ml $CH_2Cl_2$, 250 ml $CH_2Cl_2/CH_3OH$ 97/3, 1000 ml $CH_2Cl_2/CH_3OH$ 95/5, and 1000 ml $CH_2Cl_2/CH_3OH$ 90/10. Both enantiomers of BiMSuM elute in the fraction 95/5. The fractions are analyzed by HPLC ($NH_2$-column, which is able to separate the two enatiomers). Enriched fractions of one or the other enantiomer are pooled and evaporated. Analysis is carried out by $NH_2$-HPLC and $^1H$ NMR (200 MHz, $CDCl_3$):

R,S-BiMSuM/R,R-BiMSuM of enantiomeric purity 87/13: 4.5 g

R,S-BiMSuM/R,R-BiMSuM of enantiomeric purity 05/95: 0.6 g 9.2 Methyl-di-ethylsulfoxide (bis(Ethylsulfinyl)methane, BiESuM) ($=CH_3CH—SO—CH_2—SO—CH_2CH_3$)

4 ml of $CH_3CH_2—SO—CH_2—S—CH_2CH_3$ (4.45 g, 29 mmoles; Fluka 02845) are diluted at room temperature in 25 ml methanol. The solution is stirred and kept at 0C. Dropwise, 7 g $NaIO_4$ (33 mmoles) in 50 ml water are added. The reaction mixture is kept, under stirring, for 15 h at 0° C. The advancement of the reaction is controlled by thinlayer chromatography (TLC, solvent: $CH_2C_2/CH_3OH$ 90/10, detection by $I_2$, $KMnO_4$; $CH_3CH_2SOCH_2SCH_2CH_3$, Rf=0.95; $CH_3CH_2SOCH_2SOCH_2CH_3$, Rf=0.7). reaction mixture is filtered over Celite, which is rinsed with 300 ml water, 200 ml $CH_2Cl_2$, then 200 ml methanol. The aqueous phase is 3 times extracted with $CH_2Cl_2$, then with ethylacetate. The organic fractions are pooled, dried over $Na_2SO_4$, and evaporated.

The product is purified and fractions containing the two enantiomers are enriched by 3 passages over a silica column (ID 2 cm, 38 g silica in $CH_2Cl_2$) and elution with 100 ml $CH_2CO_2$, 200 ml $CH_2Cl_2/CH_3OH$ 99/1, 200 ml $CH_2Cl_2/CH_3OH$ 97/3, 200 ml $CH_2Cl_2/CH_3OH$ 95/05, 200 ml $CH_2C_2/CH_3OH$ 92.5/7.5, 200 ml $CH_2Cl_2/CH_3OH$ 90/10. Both enantiomers of BiESuM elute in the fraction 95/5. The fractions are analyzed by HPLC /(silica column, which is able to separate the two enantiomers). Enriched fractions of one or the other enantiomer are pooled and evaporated. Analysis is carried out by silica HPLC and $^1H$ NMR (200 MHz, $CDCl_3$): δ3.89 (quint., 2H, —SO—$CH_2$—SO—), 3.1 (quad., 4H, —$CH_2$—), 1.40 (t, 6H, —$CH_3$).

Fraction 1: R,S-BiESuM/R,R-BiESuM of enantiomeric purity 84/16: 1.9 g

Fraction 2: R,S-BiESuM/R,R-BiESuM of enantiomeric purity 16/84: 0.075 g

The present invention is not to be limited in scope by its specific embodiments described which are intended as single illustrations of individual aspects of the invention and any compositions and compounds which are functionally equivalent are within the scope of the invention. Indeed, various modifications of the invention in addition to those shown and described therein will become apparent to those skilled in the art from the foregoing description and accompanying drawings. Said modifications intended to fall within the scope of the appended claims. Accordingly, having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. A process for transferring a therapeutically active polynucleotide into a target cell in vitro, wherein said cell is brought into contact with a composition comprising a mixture of at least one therapeutically active polynucleotide and at least one aprotic polar compound selected from the group consisting of:

(a) formula I:

$$R_1 \underset{}{\overset{\overset{\displaystyle O}{\|}}{S}} R_2$$

wherein $R_1$ and $R_2$ are identical or different alkyl radicals of 1 to 8 carbon atoms which are optionally substituted, with the proviso that when one of $R_1$ or $R_2$ is a radical of 1 or 2 carbon atoms, the other is a radical of at least 3 carbon atoms;

wherein the volume of the aprotic polar compound represents from 5 to 50% of the total volume of the composition, and wherein the polynucleotide prior to being part of the mixture, is free of any compound which facilitates its introduction into a target cell.

2. The process of claim 1, wherein said target cell is a mammalian cell.

3. The process of claim 1, wherein said target cell is an airways cell.

4. A process according to claim 1, further comprising the step of adjusting the temperature of the composition to approximately the same temperature as the cell before bringing it into contact with the cell.

5. The process according to claim 1, wherein said aprotic polar compound is selected from the group consisting of di-n-propyl sulphoxide (DPSO), and tetramethylene sulfoxide (TEMSO).

6. The process according to claim 1, wherein said polynucleotide is an antisense polynucleotide.

7. The process according to claim 1, wherein said polynucleotide is a ribozyme.

8. The process according to claim 1, wherein said polynucleotide comprises a gene of interest and elements which enable the said gene of interest to be expressed.

9. The process according to claim 8, wherein said polynucleotide encodes all or part of a polypeptide.

10. The process according to claim 9, wherein said polypeptide is an enzyme, a hormone, a cytokine, a membrane receptor, an antibody, a factor which regulates transcription, translation or replication, a polypeptide, a polypeptide which forms a membrane channel, a transport polypeptide, an adhesion molecule or a ligand.

11. The process according to claim 1, wherein said aprotic polar compound is in aqueous solution.

12. The process according to claim 1, wherein the volume of the polar compound represents from 15 to 20% of the total volume of the composition.

13. The process according to claim 9, wherein the said polypeptide exhibits an immunogenic activity.

14. The process according to claim 1, wherein $R_1$ and $R_2$ are linked in order to cyclize the molecule.

15. The process according to claim 1, wherein said polynucleotide encodes all or part of a polypeptide.

16. The process according to claim 9, wherein the polynucleotide encodes a CFTR protein, dystrophin, factor VII or factor IX, HPV E6/E7, MUC1, BRAC1, interferon, an interleukin, tumor necrosis factor alpha, or GM-CSF.

17. The process according to claim 9, wherein the polynucleotide is a tk gene of herpes simplex virus type 1, a retinoblastoma gene or a gene for p53.

18. The process according to claim 9, wherein the polynucleotide encodes $F(ab)_2$, $Fab^1$, Fab fragments, or an anti-idiotype immunoglobulin.

* * * * *